(12) United States Patent
Chafin et al.

(10) Patent No.: US 7,468,410 B2
(45) Date of Patent: Dec. 23, 2008

(54) STABILIZATION OF POLYOLEFINS WITH LIQUID TRIS-(MONO-ALKYL)PHENYL PHOSPHITES

(75) Inventors: Laura F. Chafin, Bologna (IT); Walid Al-Akhdar, Mobile, AL (US); Sai Ping Shum, Pleasantville, NY (US); Stanley J. Padegimas, Mobile, AL (US); Roswell Easton King, Pleasantville, NY (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 139 days.

(21) Appl. No.: 11/487,839

(22) Filed: Jul. 17, 2006

(65) Prior Publication Data

US 2007/0021537 A1  Jan. 25, 2007

Related U.S. Application Data

(60) Provisional application No. 60/701,279, filed on Jul. 21, 2005.

(51) Int. Cl.
*C08K 5/524* (2006.01)

(52) U.S. Cl. .................. 524/128; 524/585; 524/587

(58) Field of Classification Search ............ 524/728, 524/585, 128, 587
See application file for complete search history.

(56) References Cited

U.S. PATENT DOCUMENTS

| | | | | |
|---|---|---|---|---|
| 2,834,798 A | * | 5/1958 | Hechenbleikner et al. ...... | 558/85 |
| 3,644,536 A | | 2/1972 | Bafford ....................... | 260/618 |
| 3,756,906 A | | 9/1973 | Leyland et al. ............... | 161/231 |
| 4,261,880 A | * | 4/1981 | Fujii et al. ................... | 524/147 |
| 4,492,661 A | * | 1/1985 | Maul et al. .................... | 558/96 |
| 4,829,112 A | | 5/1989 | Ishii et al. | |
| 5,208,368 A | | 5/1993 | Scherzer et al. ............. | 560/333 |
| 5,254,709 A | | 10/1993 | Hunter ......................... | 558/96 |
| 6,576,788 B1 | | 6/2003 | Penzel et al. ................ | 560/333 |

FOREIGN PATENT DOCUMENTS

| | | |
|---|---|---|
| DE | 2940620 | 4/1981 |
| EP | 551 062 | * 12/1992 |
| GB | 1298248 | 11/1972 |
| GB | 2227490 | 8/1990 |
| JP | 7309884 | 11/1995 |

OTHER PUBLICATIONS

Plastics Additives Handbook, 4th Ed., R. Gächter, H. Müller, Eds., 1993, pp. 40-71.
The Thompson Corp. on STN, Abstract No. 1981-29234D for DE 2940620, Apr. 16, 1981.
English Abstract for JP 7309884, Nov. 28, 1995.

* cited by examiner

*Primary Examiner*—Bernard Lipman
(74) *Attorney, Agent, or Firm*—Tyler A. Stevenson

(57) ABSTRACT

The present invention discloses a process for stabilizing polyolefin compositions against the deleterious effects of melt processing, heat aging and exposure to combustion products of natural gas, which process comprises incorporating or applying to a polyolefin an effective stabilizing amount of a tris-(mono-alkyl)phenyl phosphite ester of the formula I, (I)

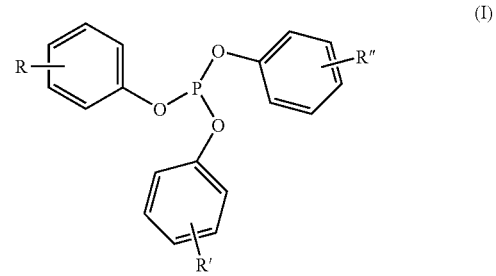

or a mixture of phosphite esters of formula I, where each R is the same or different and is straight or branched chain alkyl of from 1 to 8 carbon atoms, and where said phosphite ester or phosphite ester mixture is in the liquid state at 25° C. and 1 atm of pressure. Also disclosed is a stabilized composition comprising polyolefin and a present phosphite ester or phosphite ester mixture as well as certain mixtures of tris-(mono-alkyl)phenyl phosphite. The present liquid phosphite ester stabilizers are especially compatible with low density polyethylene.

18 Claims, No Drawings

STABILIZATION OF POLYOLEFINS WITH LIQUID TRIS-(MONO-ALKYL)PHENYL PHOSPHITES

This application claims benefit under 35 USC 119(e) of U.S. provisional application No. 60/701,279, filed Jul. 21, 2005, the contents of which are hereby incorporated by reference.

The present invention is aimed at a process for the stabilization of polyolefins with certain liquid tris-(mono-alkyl)phenyl phosphite esters or liquid mixtures of tris-(mono-alkyl)phenyl phosphite esters.

BACKGROUND

Organic phosphorus compounds are well known polymer process stabilizers. For Example, Plastics Additives Handbook, 4th Ed., R. Gaechter, H. Mueller, Eds., 1993, pages 40-71, discusses the stabilization of polypropylene (PP) and polyethylene (PE).

Known phosphite and phosphonite stabilizers include for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)phosphite, bis(2,4-di-α-cumylphenyl)pentaerythrtitol diphosphite, diisodecyl pentaerythritol diphosphite, bis(2,4-di-tert-butylphenyl)pentaerythritol diphosphite (D), bis(2,6-di-tert-butyl-4-methylphenyl)pentaerythritol diphosphite (E), bisisodecyloxy-pentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis (2,4-di-tert-butylphenyl) 4,4'-biphenylene-diphosphonite (H), 6-isooctyloxy-2,4,8,10-tetra-tert-butyl-dibenzo[d,f][1,3,2]dioxaphosphepin (C), 6-fluoro-2,4,8,10-tetra-tert-butyl-12-methyl-dibenzo[d,g][1,3,2]dioxaphosphocin (A), bis(2,4-di-tert-butyl-6-methylphenyl) methyl phosphite, bis(2,4-di-tert-butyl-6-methylphenyl) ethyl phosphite (G), 2,2',2''-nitrilo[triethyltris(3,3'5,5'-tetra-tert-butyl-1,1'-biphenyl-2,2'-diyl)phosphite] (B), bis(2,4-di-t-butylphenyl)octylphosphite, poly(4,4'-{2,2'-dimethyl-5,5'-di-t-butylphenylsulfide-}octylphosphite), poly(4,4'{-isopropylidenediphenol}-octylphosphite), poly(4,4'-{isopropylidenebis[2,6-dibromophenol]}-octylphosphite), poly(4,4'-{2,2'-dimethyl-5,5'-di-t-butylphenylsulfide}-pentaerythrityl diphosphite),

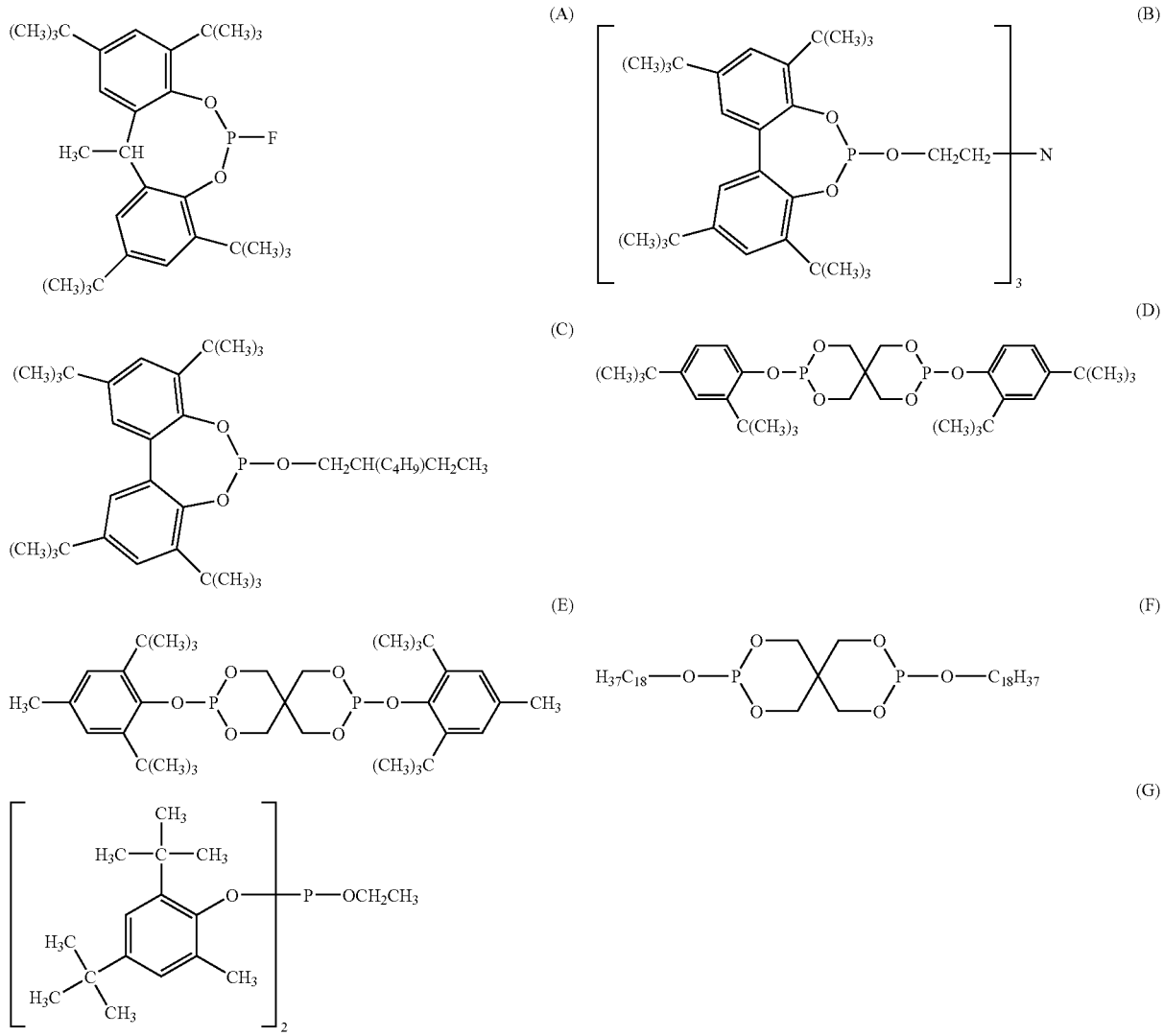

-continued

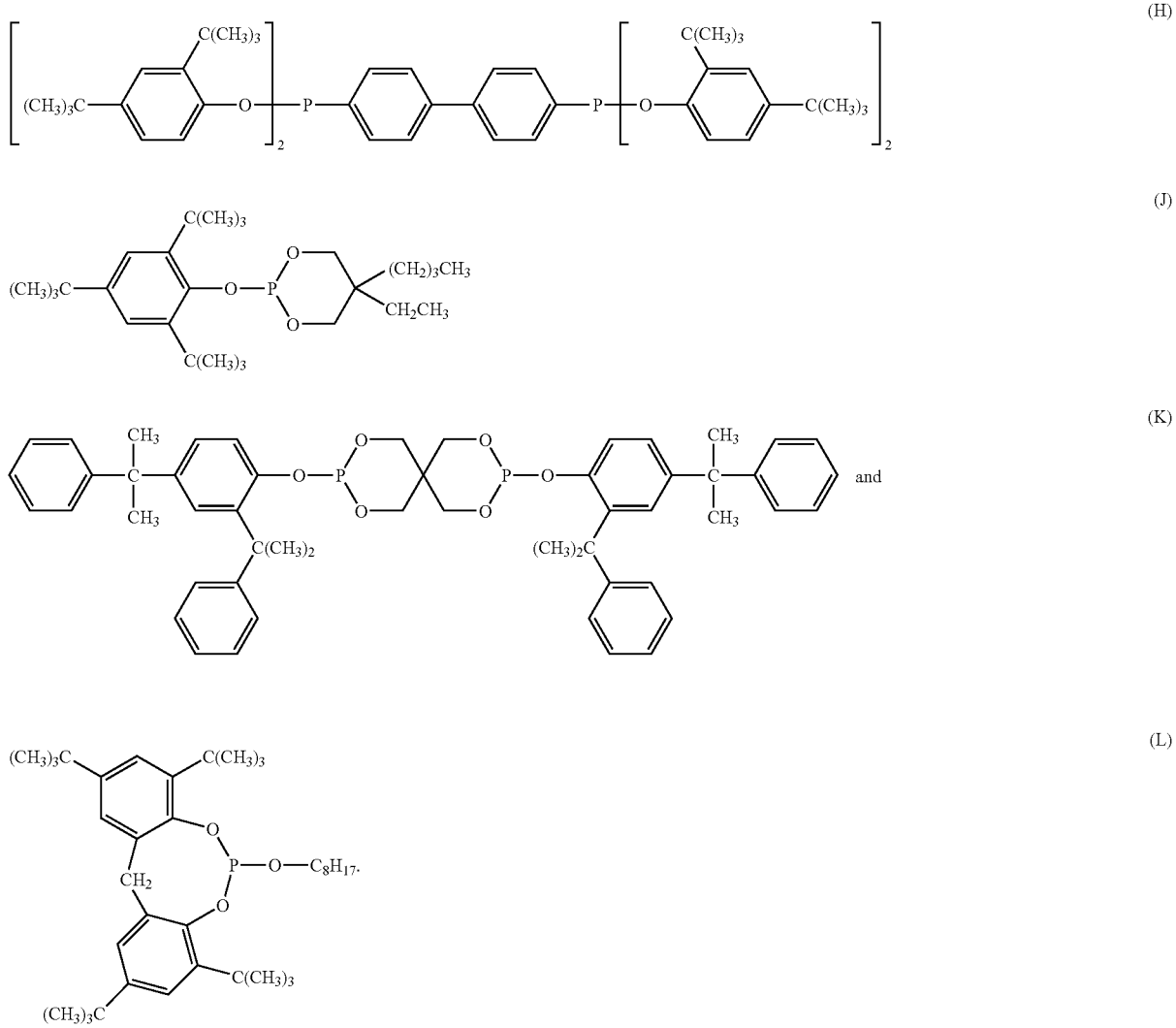

U.S. Pat. No. 3,756,906 discloses phosphite esters as stabilizers for polyester-reinforced rubbers.

U.S. Pat. Nos. 5,208,368 and 6,576,788 relate to a process for the preparation of mixtures diphenylmethane diisocyanates and polyphenylpolymethylene polyisocyanates. Aryl phosphites are taught as stabilizers.

GB2227490 discloses processing stabilizer mixtures prepared from phosphorus trichloride, biphenyl and a phenol.

GB1298248 teaches a method for the preparation of tris-peroxides. Triaryl phosphites are part of a bicomponent catalyst.

U.S. Pat. No. 3,644,536 likewise teaches a method for preparation of tris(α-hydroxyispopropyl)benzene. Tri-aryl phosphites are part of bicomponent catalyst system.

DE2940620 teaches a method for the preparation of tri-arylphosphites. The aryl group may be substituted by one or more branched alkyl or by cycloalkyl, aryl or aralkyl. The triarylphosphites are useful as polymer stabilizers.

U.S. Pat. No. 5,254,709 discloses a method for the preparation of sterically hindered aryl phosphites.

JP7309884 discloses a method for the preparation of tri-alkylphenyl phosphites.

Those in industry still seek phosphite stabilizers that are more compatible with polyolefins than those that are commercially available.

SUMMARY

It has been found that certain tris-(mono-alkyl)phenyl phosphites, or mixtures of tris-(mono)alkyphenyl phosphites, which phosphites or phosphite mixtures are in the liquid state at ambient conditions, are exceptionally compatible with polyolefins. The tris-(mono-alkyl)phenyl phosphites or the phosphite mixtures are excellent processing stabilizers.

Disclosed is a process for stabilizing a polyolefin against the deleterious effects of melt processing, heat aging and exposure to combustion products of natural gas, which process comprises incorporating into or applying to said polyolefin
an effective stabilizing amount of
a tris-(mono-alkyl)phenyl phosphite ester of the formula I

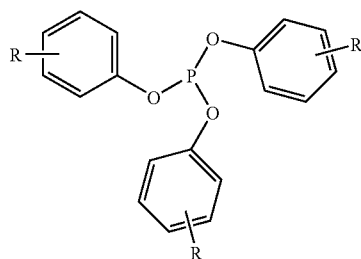

or a mixture of phosphite esters of the formula I,
where each R is the same or different and is a straight or branched chain alkyl of from 1 to 8 carbon atoms, and where said phosphite ester or mixture of phosphite esters is in the liquid state at 25° C. and 1 atm of pressure.

Also disclosed is a polyolefin composition stabilized against the deleterious effects of melt processing, heat aging and exposure to combustion products of natural gas, which composition comprises
a polyolefin and
an effective stabilizing amount of
a tris-(mono-alkyl)phenyl phosphite ester of the formula I,

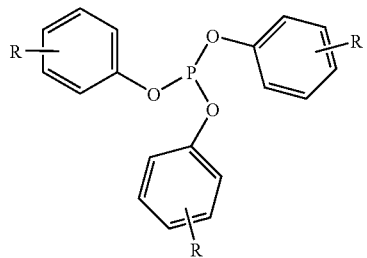

or a mixture of phosphite esters of the formula I,
where each R is the same or different and is a straight or branched chain alkyl of from 1 to 8 carbon atoms, and where said phosphite ester or mixture of phosphite esters is in the liquid state at 25° C. and 1 atm of pressure.

DETAILED DISCLOSURE

The manufacture of nonylphenol is disclosed for example in Faith, Keyes and Clark, *Industrial Chemicals*, F. A. Lowenheim, M. K. Moran, Eds., Wiley-Interscience, New York, 4$^{th}$ ed., 1975, pp. 575-578. See *Merck Index* 11,6599. This is representative of the manufacture of alkylphenols.

Tris-(mono-alkyl)phenyl phosphites are prepared by reacting three equivalents of mono-alkylphenol with phosporus trichloride in the absence of oxygen, for example under a nitrogen atmosphere, and in the presence of an acid scavenger such as triethylamine.

Alkyl is linear or branched and is for example methyl, ethyl, n-propyl, isopropyl, n-butyl, sec-butyl, isobutyl, tert-butyl, pentyl, tert-amyl, hexyl, heptyl, 2,4,4-trimethylpentyl, 2-ethylhexyl n-octyl or tert-octyl.

Alkyl is for example straight or branched chain alkyl 1 to 6 carbon atoms or of 1 to 4 carbon atoms.

For example, alkyl is methyl, ethyl, sec-butyl, t-amyl or hexyl.

The phosphite ester or mixture of phosphite esters of formula I of this invention are necessarily liquid at ambient conditions, 25° C. and 1 atmosphere of pressure. Otherwise the only limitation is that each R is a straight or branched chain alkyl of 1 to 8 carbon atoms.

In the present mixtures of phosphite esters of formula I, the individual components need not be liquid in the pure (isolated) state.

For example, pure tris-2-t-butylphenylphosphite (mp 66-68° C.) and tris-4-t-butylphenylphosphite (mp 73-75° C.) are excluded from this invention as individual phosphite esters. These compounds are not excluded from the present phosphite ester liquid mixtures.

Tris-3-t-butylphenylphosphite (bp 193-198° C. at 0.02 mm) and tris-2-sec-butylphenylphosphite (bp 160-165° C. at 0.01 mm) are included in this invention as individual phosphite esters.

A liquid mixture of phosphite esters may be prepared by mixing two or more pure phosphite esters, or may be prepared directly from phosphorus trichloride using a mixture of two or more different mono-alkylphenols.

In a present mixture of phosphite esters, there are at least two different phosphite esters of formula I. Two phosphite esters are different by virtue of having a different alkyl or differently substituted alkyl on at least one of the phenyl groups.

A different alkyl means a different chain length or a different chain branching (e.g. n-butyl, t-butyl, sec-butyl). Differently substituted means different positions (e.g. meta, para) relative to the phenolic hydroxyl.

Of course, two different mono-alkylphenols may have alkyls of both different chain length and different position, or may have alkyls of both different branching and different position, or may have alkyls of both different chain length and different branching, or may have alkyls of different chain length, different branching and different position.

Advantageously, the present liquid phosphite mixture is where the phenolic groups are about 60% or greater ortho substituted. For example, the phenolic groups are about 70% or greater ortho substituted, or are about 80% or greater ortho substituted. The remainder may be for example para substituted.

For example, each of the R groups are equivalent, for example each are sec-butyl, and are in the ortho and para positions.

For example, the phosphite ester mixture is a mixture of the compounds

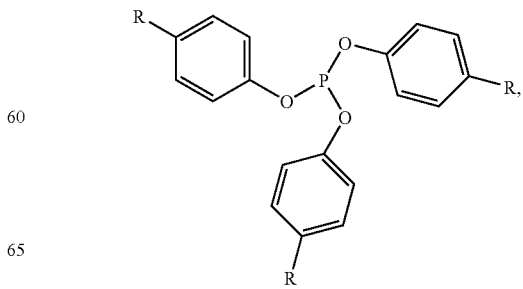

-continued

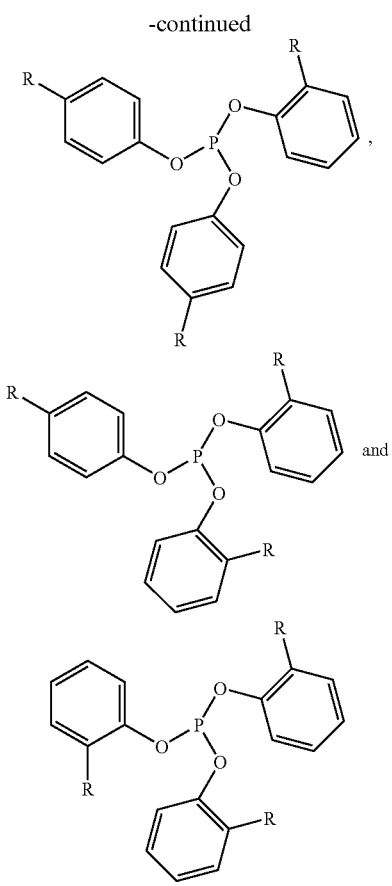

where the R groups are equivalent.

For example, in the present phosphite ester mixtures, each R group is equivalent and the phenolic groups are about 60% or greater ortho substituted. For example, the phenolic groups are about 70% or greater ortho substituted, or are about 80% or greater ortho substituted, the remainder being para substituted.

The present liquid phosphite ester mixtures are also a subject of the present invention.

Accordingly, also subject of this invention is a mixture of tris-(mono-alkyl)phenyl phosphite esters of formula I,

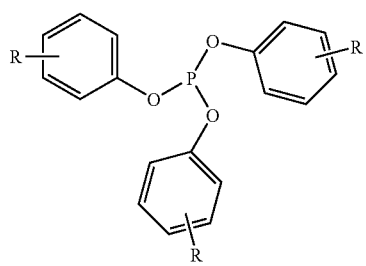

(I)

where each R is the same or different and is straight or branched chain alkyl of from 1 to 8 carbon atoms, and where the mixture of phosphite esters is in the liquid state at 25° C. and 1 atm of pressure.

Examples for polyolefins are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1.), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1.) with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

Polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers. Preferred polyolefins of the present invention include polypropylene homopolymers, polypropylene impact (heterophasic) copolymers, blends thereof, and TPO's such as blends of polypropylene homopolymers and impact copolymers with EPDM or ethylene-alpha-olefin copolymers.

In particular, the present polyolefins are low density polyethylene (LDPE).

Melt processing techniques are know and include for example extrusion, co-kneading, pultrusion, injection molding, co-extrusion, fiber extrusion, fiber spinning, film extrusion (cast, blown, blowmolding), rotational molding, and the like.

The present tris-(mono-alkyl)phenyl phosphite esters are used for example, in amounts of from about 0.01% to about 5% by weight, based on the weight of the polyolefin, from about 0.025% to about 1%, from about 0.05% to about 0.5% by weight, from about 0.01% to about 1%, about 0.01% to about 0.5%, about 0.025% to about 5%, or about 0.05% to about 5% by weight, based on the weight of the polyolefin to be stabilized. For example, the present tris-(mono-alkyl)phenyl phosphite esters are present at a level of less than about 3% by weight, based on the weight of the polyolefin, or from about 0.01% to about 2.5% by weight, or from about 0.01% to about 2% by weight, based on the weight of the polyolefin.

The incorporation of the present tris-(mono-alkyl)phenyl phosphite esters and optional further additives into the polyolefin is carried out by known methods, for example before or after molding or also by applying the dissolved or dispersed stabilizer or stabilizer mixture to the polyolefin, with or without subsequent evaporation of the solvent. The stabilizer or stabilizer mixture can also be added to the polyolefins to be stabilized in the form of a masterbatch which contains the present phosphite esters and optional additives in a concentration of, for example, about 2.5% to about 60% by weight.

The tris-(mono-alkyl)phenyl phosphite esters and optional further additives can also be added before or during the polymerization or before crosslinking.

The present tris-(mono-alkyl)phenyl phosphite esters and optional further additives can be incorporated into the polyolefin to be stabilized in pure form or encapsulated in waxes, oils or polymers.

The present tris-(mono-alkyl)phenyl phosphite esters and optional further additives can also be sprayed onto the polyolefin to be stabilized. It is able to dilute other additives (for example other conventional additives discussed further) or their melts so that it can be sprayed also together with these additives onto the polyolefin to be stabilized. Addition by spraying during the deactivation of the polymerization catalysts is particularly advantageous, it being possible to carry out spraying using, for example, the steam used for deactivation.

In the case of spherically polymerized polyolefins it may, for example, be advantageous to apply the present stabilizers optionally together with other additives, by spraying.

The polyolefin compositions according to the instant invention are useful in the manufacture of polyolefin articles. The said articles are for example woven fibers, non-woven fibers, films, sheets or molded articles.

Further stabilizers include for example hindered phenolic antioxidants, hindered amine light stabilizers, hydroxylamine stabilizers, amine oxide stabilizers, benzofuranone stabilizers and other organic phosphorus stabilizers.

Hindered phenolic antioxidants include for example tris(3,5-di-tert-butyl-4-hydroxybenzyl)isocyanurate, 1,3,5-tris-(3,5-di-tert-butyl-4-hydroxybenzyl)-2,4,6-trimethylbenzene, the calcium salt of the monoethyl ester of 3,5-di-tert-butyl-4-hydroxybenzylphosphonic acid, pentaerythritol tetrakis [3-(3,5-di-tert-butyl-4-hydroxyphenyl)propionate] or octadecyl 3-(3,5-di-tert-butyl-4-hydroxyphenyl)propionate.

Hindered amine light stabilizers include for example the condensate of 1-(2-hydroxyethyl)-2,2,6,6-tetramethyl-4-hydroxypiperidine and succinic acid,

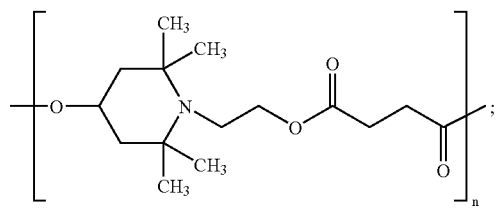

linear or cyclic condensates of N,N'-bis(2,2,6,6-tetramethyl-4-piperidyl)-hexamethylenediamine and 4-tert-octylamino-2,6-dichloro-1,3,5-triazine,

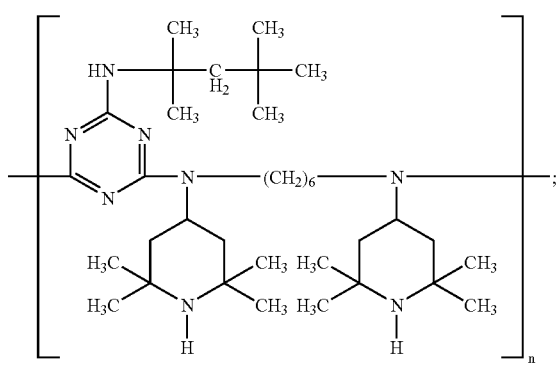

the condensate of 2-chloro-4,6-di-(4-n-butylamino-1,2,2,6,6-pentamethylpiperidyl)-1,3,5-triazine and 1,2-bis-(3-aminopropylamino)ethane,

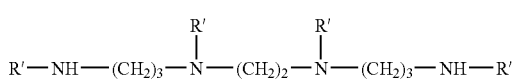

where R' is

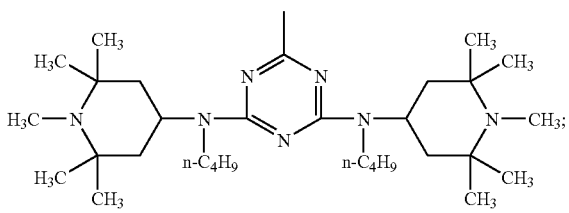

the oligomeric compound which is the condensation product of 4,4'-hexamethylene-bis (amino-2,2,6,6-tetramethylpiperidine) and 2,4-dichloro-6-[(2,2,6,6-tetramethylpiperidin-4-yl)butylamino]-s-triazine end-capped with 2-chloro-4,6-bis(dibutylamino)-s-triazine,

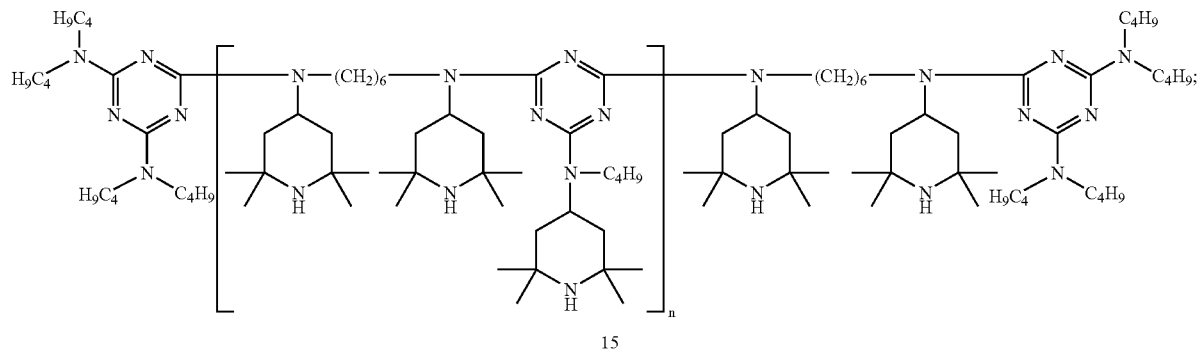

product obtained by reacting a product, obtained by reacting 1,2-bis(3-amino-propylamino) ethane with cyanuric chloride, with (2,2,6,6-tetramethylpiperidin-4-yl)butylamine,

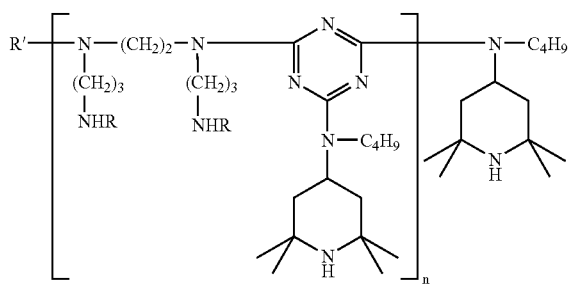

where R'=R or H
and where R=

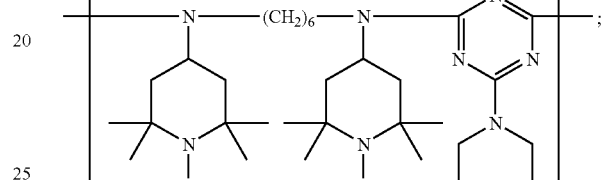

linear or cyclic condensates of N,N'-bis-(2,2,6,6-tetramethyl-4-piperidyl)-hexamethylenediamine and 4-morpholino-2,6-dichloro-1,3,5-triazine,

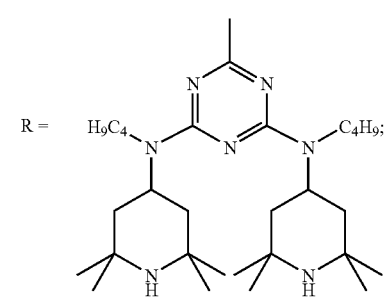

linear or cyclic condensates of N,N'-bis-(1,2,2,6,6-pentamethyl-4-piperidyl)-hexamethylenediamine and 4-morpholino-2,6-dichloro-1,3,5-triazine,

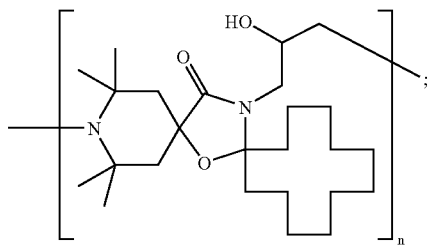

a reaction product of 7,7,9,9-tetramethyl-2-cycloundecyl-1-oxa-3,8-diaza-4-oxospiro[4,5]decane and epichlorohydrin,

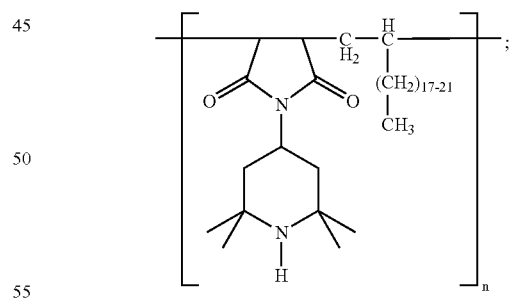

reaction product of maleic acid anhydride-$C_{18}$-$C_{22}$-α-olefin-copolymer with 2,2,6,6-tetramethyl-4-aminopiperidine,

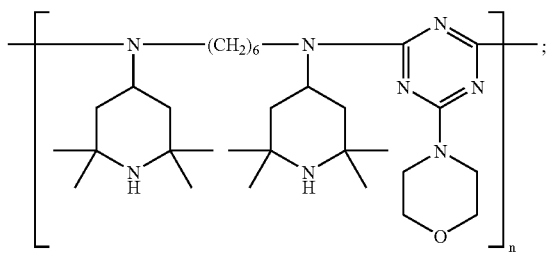

the reaction product of 2,4-bis[(1-cyclohexyloxy-2,2,6,6-piperidin-4-yl)butylamino]-6-chloro-s-triazine with N,N'-bis(3-aminopropyl)ethylenediamine),

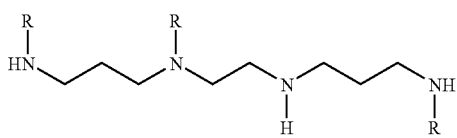

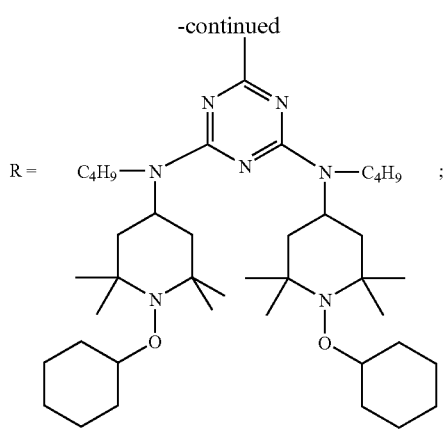

the oligomeric compound which is the condensation product of 4,4'-hexamethylenebis(amino-1-propoxy-2,2,6,6-tetramethylpiperidine) and 2,4-dichloro-6-[(1-propoxy-2,2,6,6-tetramethyl-piperidin-4-yl)butylamino]-s-triazine end-capped with 2-chloro-4,6-bis(dibutylamino)-s-triazine,

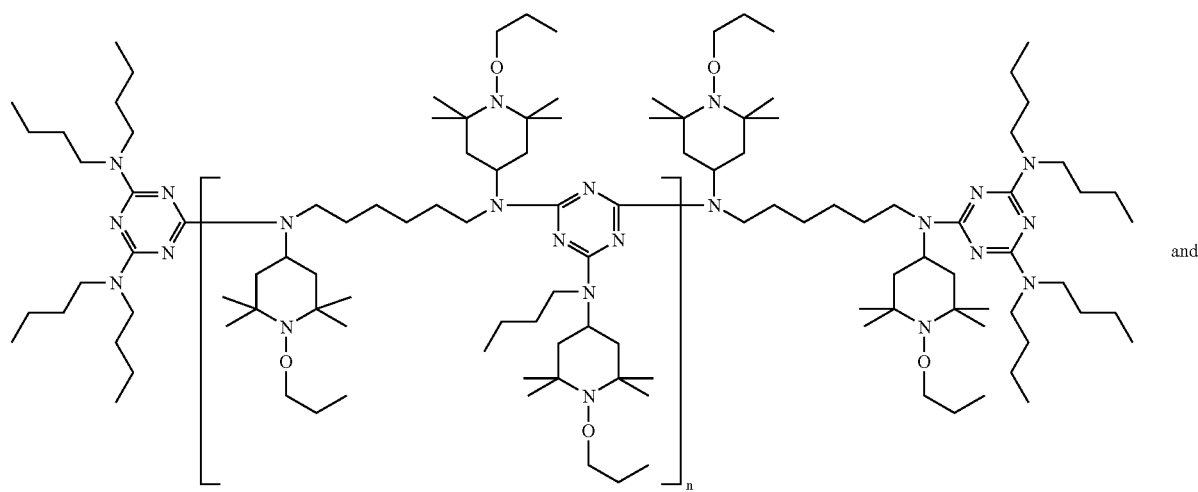

and the oligomeric compound which is the condensation product of 4,4'-hexamethylenebis(amino-1,2,2,6,6-pentaamethylpiperidine) and 2,4-dichloro-6-[(1,2,2,6,6-pentaamethylpiperidin-4-yl)butylamino]-s-triazine end-capped with 2-chloro-4,6-bis(dibutylamino)-s-triazine,

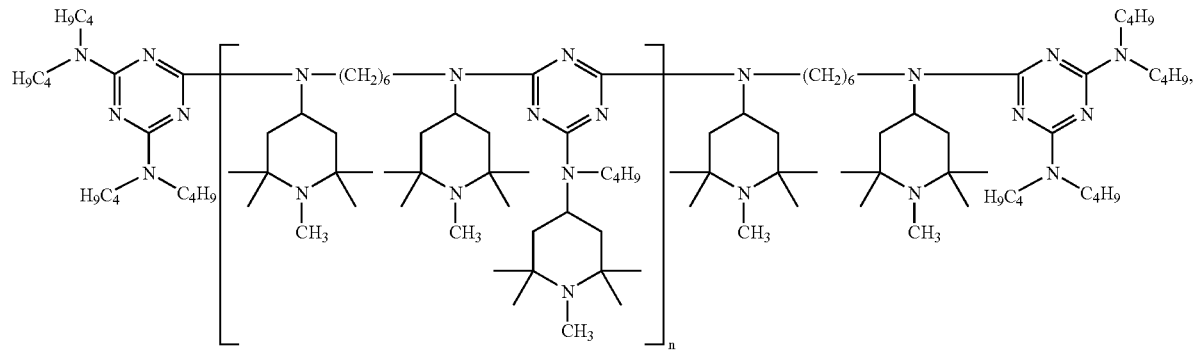

where n is an integer such that the total molecular weight is above about 1000 g/mole.

Hydroxylamine stabilizers are for example N,N-dibenzylhydroxylamine, N,N-diethylhydroxylamine, N,N-dioctylhydroxylamine, N,N-dilaurylhydroxylamine, N,N-didodecylhydroxylamine, N,N-ditetradecylhydroxylamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, N-methyl-N-octadecylhydroxylamine or N,N-di(hydrogenated tallow)hydroxylamine.

The amine oxide stabilizer is for example GenoX™ EP, a di($C_{16}$-$C_{18}$)alkyl methyl amine oxide, CAS# 204933-93-7.

Benzofuranone stabilizers are for example 3-(4-(2-acetoxyethoxy)phenyl)-5,7-di-tert-butyl-benzofuran-2-one, 5,7-di-tert-butyl-3-(4-(2-stearoyloxyethoxy)phenyl)benzofuran-2-one, 3,3'-bis(5,7-di-tert-butyl-3-(4-(2-hydroxyethoxy)phenyl)benzofuran-2-one), 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one or 3-(2,3-dimethylphenyl)-5,7-di-tert-butyl-benzofuran-2-one.

Further organic phosphorus stabilizers are for example those as disclosed previously. Further organic phosphorus stabilizers are also for example those as disclosed in U.S. Pat. No. 6,541,549 and U.S. Pat. app. No. 2003/0096890, the disclosures of which are hereby incorporated by reference.

These optional stabilizers are employed at the same levels as the present tris-(mono-alkyl)phenyl phosphite esters.

In addition to the tris-(monoalkyl)phenyl phosphite esters and the above optional stabilizers, the following further additives may also be employed. These further stabilizers are employed for example at use levels from about 0.01% to about 5% by weight, based on the weight of the polyolefin.

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl)sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl)isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxy-benzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)ox-amide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3, 5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N, N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,pα-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyidiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6, 6-tetramethylpiperid-4-yl)-sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987, 5,977,219 and 6,166,218 such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3, 5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl) phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H- benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3, 5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl 5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3, 5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS# 7443-25-6), and Sanduvor® PR31, di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl)sebacate, bis(2,2,6,6-tetramethyl-4-piperidyl) succinate, bis(1,2,2,6,6-pentamethyl-4-piperidyl)sebacate, bis(1-octyloxy-2,2,6,6-tetramethyl-4-piperidyl)sebacate, bis (1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6, 6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6, 6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5] decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5] decane, a reaction product of 7,7,9,9-tetramethyl-2-cycloundecyl-1-oxa-3,8-diaza-4-oxospiro [4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2, 2,6,6-pentamethyl-4-aminopiperidine.

The sterically hindered amine may also be one of the compounds described in U.S. Pat. No. 5,980,783, the relevant parts of which are hereby incorporated by reference, that is compounds of component 1-a), 1-b), 1-c), 1-d), 1-e), 1-f), 1-g), 1-h), 1-i), 1-j), 1-k) or 1-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2, or 1-k-1 listed on columns 64-72 of said U.S. Pat. No. 5,980,783.

The sterically hindered amine may also be one of the compounds described in U.S. Pat. Nos. 6,046,304 and 6,297,299, the disclosures of which are hereby incorporated by reference, for example compounds as described in claims 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine,1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine,1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4- yl)sebacate, bis(1-(2-hydroxy-2-methylpropoxy)-2,2,6,6-tetramethylpiperidin-4-yl)adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl)glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,736,597; 5,942,626; 5,959,008; 5,998,116; 6,013,704; 6,060,543; 6,187,919; 6,242,598 and 6,468,958, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy-4-(2-hydroxy-4-(2-hydroxy-ethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxypropyloxy)-phenyl]-s-triazine, 2,4-bis(2,4-dimethylphenyl)-6-[2-hydroxy-4-(3-benzyloxy-2-hydroxy-propyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)-phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethyl-phenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl)ethyl phosphite, 2,2',2"-nitrilo[triethyltris(3, 3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl)phosphite, tris(nonylphenyl) phosphite,

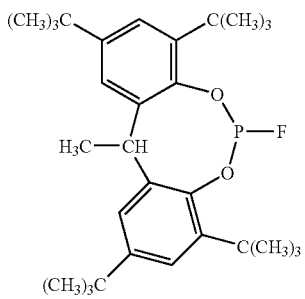

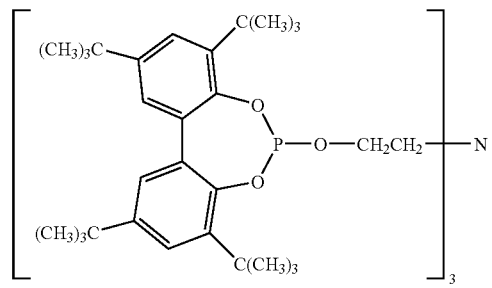

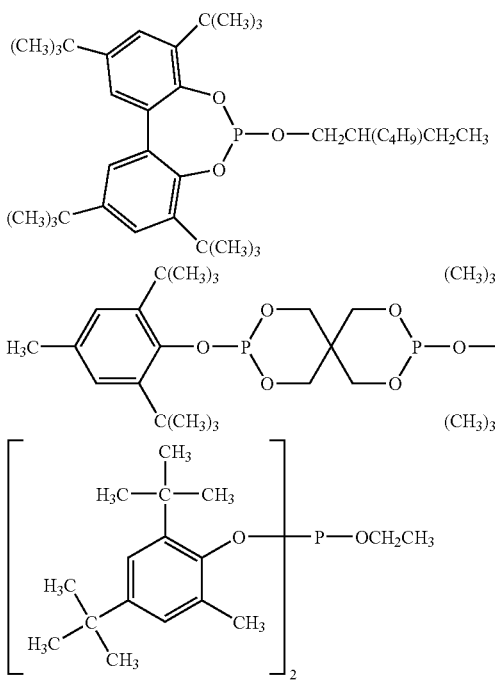
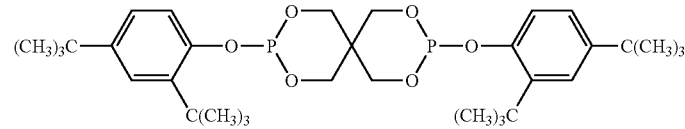
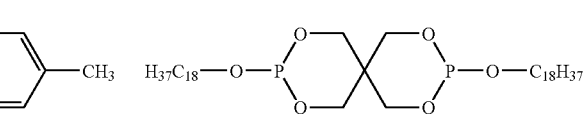
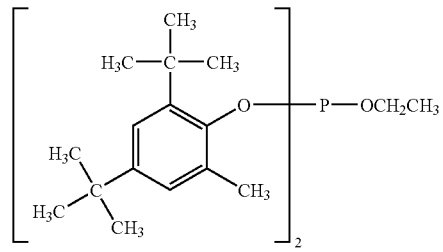

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecyinitrone, N-octadecyl-α-heptadecylnitrone, N-hexadecyl-α-heptadecyinitrone, N-ocatadecyl-α-pentadecyinitrone, N-heptadecyl-α-heptadecylnitrone, N-octadecyl-α-hexadecylnitrone, N-methyl-α-heptadecylnitrone and the nitrone derived from N,N-dialkylhydro-xylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. Nos. 4,325,863, 4,338,244, 5,175,312, 5,216,052, 5,252,643 5,369,159 5,356,966 5,367,008 5,428,177 or 5,428,162 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one. p 9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

11. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

12. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

13. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

14. Dispersing Agents, such as polyethylene oxide waxes or mineral oil.

15. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bis-benzylidene sorbitols, benzoxazinone UV absorbers such as 2,2'-p-phenylene-bis(3,1-benzoxazin-4-one), Cyasorb® 3638 (CAS# 18600-59-4), and blowing agents.

The fillers and reinforcing agents (item 13 in the list), for example talc, calcium carbonate, mica or kaolin, are added to the polyolefins in concentrations of about 0.01% to about 40% by weight, based on the overall weight of the polyolefins to be stabilized.

The fillers and reinforcing agents (item 13 in the list), for example metal hydroxides, especially aluminum hydroxide or magnesium hydroxide, are added to the polyolefins in concentrations of about 0.01% to about 60% by weight, based on the overall weight of the polyolefins to be stabilized.

Carbon black as filler is added to the polyolefins in concentrations, judiciously, of from about 0.01% to about 5% by weight, based on the overall weight of the polyolefins to be stabilized.

Glass fibers as reinforcing agents are added to the polyolefins in concentrations, judiciously, of from about 0.01% to about 20% by weight, based on the overall weight of the polyolefins to be stabilized.

The following Examples illustrate the invention in more detail. Parts and percentages are by weight unless otherwise indicated.

EXAMPLE 1

Preparation of tris-(sec-butylphenyl)phosphite Mix with triethylamine (TEA) as HCl-Scavenger To a solution of 45.0 g (0.30 mole) of a mixture of o- and p-sec-butylphenols (70% ortho and 30% para; Schenectady International) and 35.7 g (0.35 mole) of TEA in 300 mL of xylenes (isomeric mix) kept under a nitrogen atmosphere, 14.5 g (0.10 mole) of phosphorus trichloride is added at 25° C. over 2 hours. The reaction mass is heated to 65° C. to insure completion of reaction, cooled, filtered and the xylenes stripped at reduced pressure. The pale yellow liquid that remains (95% yield) analyzed by HPLC as a mix of sec-butylphenyl phosphites with only a trace of the starting phenols present; this is confirmed by P31-NMR.

EXAMPLE 2

Preparation of tris-(sec-butylphenyl)phosphite Mix

Phosphorus trichloride (98.1 g, 0.71 mole) is added at 40-45° C. over 90 min to 304.9 g (2.03 mole) of sec-butylphenols (70% ortho and 30% para; Schenectady International) that contains a catalytic amount (1.5 g, 0.015 mole) of TEA. With a nitrogen sparge to remove HCl, the reaction mass is heated to 80° C. and held at temperature for 4 hours. It is then adjusted to a pH≧8 with TEA, cooled, and filtered to yield (98%) a clear, almost colorless liquid that is (HPLC) 97% sec-butylphosphites.

The formulations in the Examples employ the following compounds:

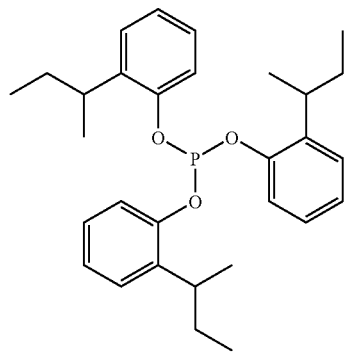

Phos 1

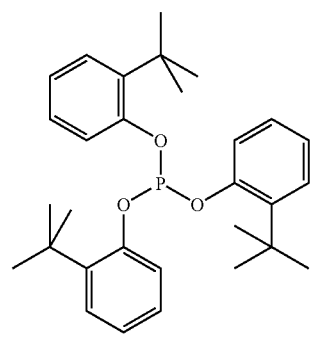

Phos 2

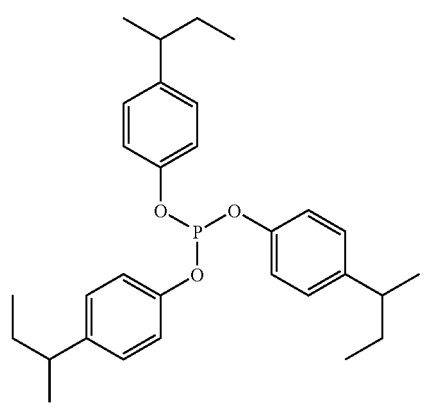

Phos 3

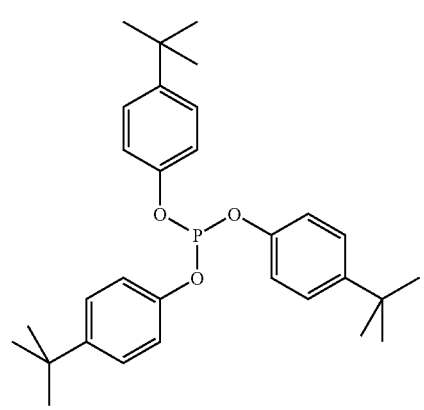

Phos 4

Phos 5

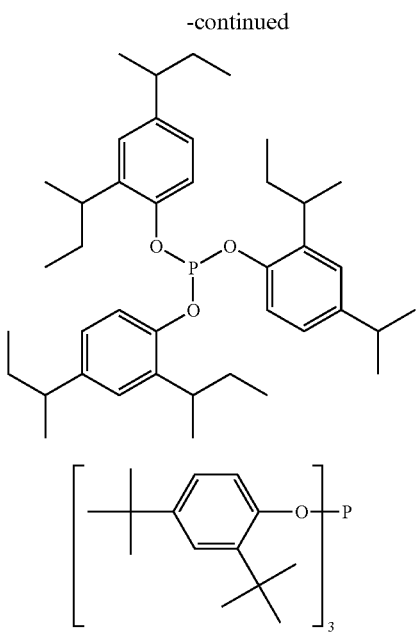

Phos 6

EXAMPLE 3

A film grade linear low density polyethylene (LL 1018; ExxonMobil) essentially free of any stabilization additives is dry blended with the base stabilization and the test additives. The base stabilization includes 500 ppm of a phenolic antioxidant, Irganox® 1076, and 800 ppm of a polymer processing aid, Dynamar FX-5920A. The test additives are added on a molar equivalent basis (42.5 ppm phosphorus). The formulations are initially melt compounded in a twin screw extruder at 190° C. under nitrogen; corresponding to the zero pass extrusion. The resultant extrudate is then multiple pass extruded on a single screw extruder, fitted with a Maddock mixing section, at 260° C. Samples of first, third and fifth pass extrudate are collected for testing. Plaques (125 mil) are prepared by compression molding of zero, first, third and fifth pass extrudate at 380° F. with 3 minutes each of low pressure, then high pressure, and then cooling. The specimens are tested for melt flow rate retention (according to ASTM-1238; 190° C./2.16 kg; 21.6 kg), color development during extrusion, and color development during exposure to oxides of nitrogen at 60° C. (according to ASTM-1925). The results are shown below. Additives are reported in weight percent based on the polymer.

| Formulation | None | Phos 1 | Phos 2 | Phos 3 | Phos 4 | Phos 5 | Phos 6 |
|---|---|---|---|---|---|---|---|
| Phosphite (ppm) | 0 | 657 | 657 | 657 | 657 | 888 | 888 |
| Melt Flow Rate; 190° C.; 2.16 kg | | | | | | | |
| Zero | 0.88 | 1.04 | 1.01 | 1.03 | 0.96 | 1.02 | 1.03 |
| 1st | 0.83 | 1.01 | 0.98 | 1.02 | 0.90 | 1.02 | 0.99 |
| 3rd | 0.76 | 0.97 | 0.88 | 0.97 | 0.75 | 0.95 | 0.88 |
| 5th | 0.65 | 0.93 | 0.78 | 0.90 | 0.67 | 0.85 | 0.84 |

| Formulation | None | Phos 1 | Phos 2 | Phos 3 | Phos 4 | Phos 5 | Phos 6 |
|---|---|---|---|---|---|---|---|
| Melt Flow Rate Data; 190° C.; 21.6 kg | | | | | | | |
| Zero | 16.50 | 17.07 | 16.94 | 16.73 | 16.93 | 16.96 | 16.92 |
| 1st | 16.12 | 17.18 | 16.83 | 16.88 | 16.56 | 17.01 | 16.86 |
| 3rd | 15.77 | 16.79 | 16.39 | 17.02 | 15.69 | 16.80 | 16.52 |
| 5th | 15.36 | 16.79 | 15.81 | 16.85 | 15.22 | 16.49 | 16.13 |
| Melt Flow Ratio; 190° C.; 21.6/2.16 kg | | | | | | | |
| Zero | 18.71 | 16.36 | 16.78 | 16.23 | 17.72 | 16.57 | 16.49 |
| 1st | 19.45 | 16.93 | 17.22 | 16.59 | 18.36 | 16.66 | 17.08 |
| 3rd | 20.74 | 17.37 | 18.69 | 17.50 | 20.86 | 17.77 | 18.69 |
| 5th | 23.77 | 18.05 | 20.33 | 18.65 | 22.81 | 19.30 | 19.32 |

As can be seen in this extrusion pass vs. melt flow rate retention table, the liquid sec-butyl substituted phosphites consistently provide better performance in comparison to their solid tert-butyl counterparts. Since the concentrations are equivalent in each of the comparisons, and since the steric hindrance is roughly the same, the performance benefit coming from the liquid state of the sec-butyl substituted phosphites is apparent.

| Formulation | None | Phos 1 | Phos 2 | Phos 3 | Phos 4 | Phos 5 | Phos 6 |
|---|---|---|---|---|---|---|---|
| Phosphite (ppm) | 0 | 657 | 657 | 657 | 657 | 888 | 888 |
| YI Color Data; C Illuminant; 2° Observer | | | | | | | |
| Zero | 2.02 | 1.05 | 1.15 | 1.21 | −0.08 | 0.30 | 1.46 |
| 1st | 4.10 | 2.50 | 2.87 | 2.50 | 1.00 | 2.25 | 3.76 |
| 3rd | 6.99 | 4.66 | 5.03 | 4.93 | 3.25 | 6.10 | 6.45 |
| 5th | 8.82 | 6.15 | 6.65 | 6.05 | 3.83 | 7.68 | 7.80 |

As can be seen in this extrusion pass vs. yellowness index color retention table, the liquid sec-butyl substituted phosphites Phos 1 and Phos 5 provide lower color than their solid t-butyl counterparts, Phos 2 and Phos 6. Since the concentrations are equivalent in each of the comparisons, and since the steric hindrance is roughly the same, the performance benefit coming from the liquid sec-butyl substituted phosphites is apparent.

| Formulation | None | Phos 1 | Phos 2 | Phos 3 | Phos 4 | Phos 5 | Phos 6 |
|---|---|---|---|---|---|---|---|
| Phosphite (ppm) | 0 | 657 | 657 | 657 | 657 | 888 | 888 |
| Gas Fade Aging; 60° C.; 1st Pass; | | | | | | | |
| 0 days | 1.40 | 1.30 | 1.29 | 1.28 | 1.22 | 1.30 | 1.34 |
| 7 days | 4.50 | 1.72 | 2.27 | 2.08 | 5.71 | 1.71 | 2.31 |
| 14 days | 6.17 | 2.16 | 2.89 | 3.16 | 8.25 | 2.40 | 2.80 |
| 21 days | 7.40 | 2.71 | 3.31 | 3.72 | 8.07 | 3.07 | 3.31 |

As can be seen in this yellowness index color retention during exposure to oxides of nitrogen table, the liquid sec-butyl substituted phosphites consistently provide lower color than their solid t-butyl counterparts. Since the concentrations are equivalent in each of the comparisons, and since the steric hindrance is roughly the same, the performance benefit coming from the liquid sec-butyl substituted phosphites is apparent.

EXAMPLE 4

Viscosity

Viscosities are measured as follows: Peltier plate, 40 mm steel cone, 2° angle 2° C./min ramp, shear stress=10 Pa.

| Sample ID | Viscosity (mPa · s) | | | | | |
|---|---|---|---|---|---|---|
| | 2° C. | 20° C. | 40° C. | 60° C. | 80° C. | 100° C. |
| P7 | 140,000 | 10,800 | 1250 | 254 | 79.1 | 33.5 |
| P8 | 1,119 | 199 | 51.6 | 19.9 | 10.0 | — |
| Phos 3 | 1,486 | 244 | 58.1 | 21.9 | 10.9 | 6.6 |

P7 is tris-nonylphenylphosphite
P8 is 70% Phos 1/30% Phos 3

Phosphites P8 and Phos 3, of the present invention, are much less viscous than a phosphite not of the present invention, P7. The lower viscosity allows for greater ease of handling.

For example, the present compounds exhibit a viscosity of less than about 1000 mPa·sec at 20° C., or less than about 750 mPa·sec at 20° C., or less than about 150 mPa·s at 40° C. or less than about 135 mPa·s at 40° C.; as measured on a TA Instruments AR-2000N cone/plate rheometer: 40 mm 2° steel cone with peltier plate, constant 10 Pa shear stress, 2° C./min. temperature ramp from 0C to 100° C.

What is claimed is:

1. A process for stabilizing a polyolefin against the deleterious effects of melt processing, heat aging and exposure to combustion products-of natural gas, which process comprises
   incorporating into or applying to said polyolefin
   an effective stabilizing amount of a mixture of at least two different
   tris-(mono-alkyl)phenyl phosphite esters of the formula I,

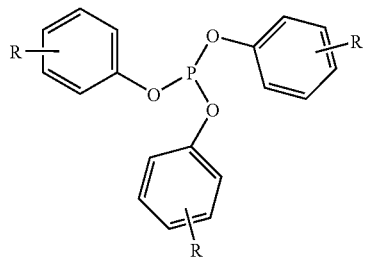

(I)

where each R is the same or different and is a straight or branched chain alkyl of from 1 to 8 carbon atoms, and where said mixture of phosphite esters is in the liquid state at 25° C. and 1 atm of pressure.

2. A process according to claim 1 where each R is the same or different and is a straight or branched chain alkyl of from 1 to 6 carbon atoms.

3. A process according to claim 1 where each R is the same or different and is a straight or branched chain alkyl of from 1 to 4 carbon atoms.

4. A process according to claim 1 where each R is substituted in the ortho or para positions and is independently methyl, ethyl, sec-butyl, t-amyl or hexyl.

5. A process according to claim 1 where each R is equivalent and is substituted in the ortho or para positions.

6. A process according to claim 1 where each R is sec-butyl and is substituted in the ortho or para positions.

7. A process according to claim 1 comprising incorporating or applying a mixture of phosphite esters of the formula I where the R groups are in the ortho or para positions and are independently methyl, ethyl, sec-butyl, t-amyl or hexyl and where the phenolic groups are about 60% or greater ortho substituted.

8. A process according to claim 1 comprising incorporating or applying a mixture of phosphite esters of the formula I where each R is equivalent and is substituted in the ortho or para positions and where the phenolic groups are about 60% or greater ortho substituted.

9. A process according to claim 1 comprising incorporating or applying a mixture of phosphite esters of formula I, where each R is sec-butyl and is substituted in the ortho or para positions and where the phenolic groups are about 60% or greater ortho substituted.

10. A process according to claim 1 where the mixture of esters are incorporated or applied at a level of from about 0.01% to about 5% by weight, based on the weight of the polyolefin.

11. A process according to claim 1 where the mixture of esters are incorporated or applied at a level of less than about 3% by weight, based on the weight of the polyolefin.

12. A process according to claim 1 comprising incorporating or applying a further stabilizer selected from the group consisting of hindered phenolic antioxidants, hydroxylamines, benzofuranones, other organic phosphorus stabilizers, sterically hindered amine light stabilizers and hydroxyphenylbenzotriazole, tris-aryl-s-triazine or hydroxyphenylbenzophenone ultraviolet light stabilizers.

13. A process according to claim 1 where the polyolefin is polyethylene.

14. A process according to claim 1 where the polyolefin is low density polyethylene.

15. A polyolefin composition stabilized against the deleterious effects of melt processing, heat aging and exposure to combustion products of natural gas, which composition comprises
   a polyolefin and
   an effective stabilizing amount of a mixture of at least two different
   tris-(mono-alkyl)phenyl phosphite esters of the formula I,

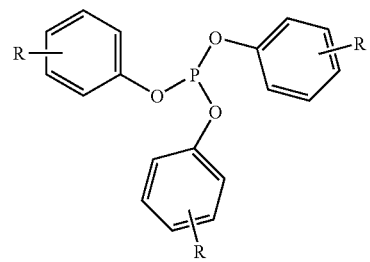

(I)

where each R is the same or different and is a straight or branched chain alkyl of from 1 to 8 carbon atoms, and where said or mixture of phosphite esters is in the liquid state at 25° C. and 1 atm of pressure.

16. A mixture of at least two different tris-(mono-alkyl) phenyl phosphite esters of formula I,

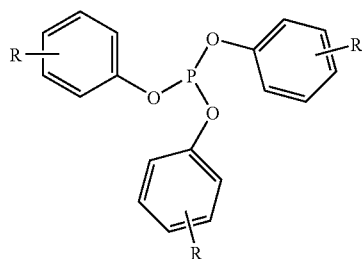

(I)

where each R is the same or different and is straight or branched chain alkyl of from 1 to 8 carbon atoms, and where the mixture of phosphite esters is in the liquid state at 25° C. and 1 atm of pressure.

17. A mixture according to claim 16 where each R is the same or different and is a straight or branched chain alkyl of from 1 to 6 carbon atoms.

18. A mixture according to claim 16 where each R is the same or different and is a straight or branched chain alkyl of from 1 to 4 carbon atoms.

* * * * *